United States Patent [19]

Brown

[11] Patent Number: 4,547,364

[45] Date of Patent: Oct. 15, 1985

[54] HAIR TREATMENT PRODUCT

[76] Inventor: Robert L. Brown, 1321 N. Nursery Rd. #115C, Irving, Tex. 75061

[21] Appl. No.: 468,695

[22] Filed: Feb. 22, 1983

[51] Int. Cl.⁴ ..................... A61K 7/06; A61K 35/78
[52] U.S. Cl. .................... 424/70; 424/195.1; 514/2; 514/167; 514/458; 514/474; 514/517
[58] Field of Search ........................................ 424/70

[56] References Cited

U.S. PATENT DOCUMENTS 3,943,234 3/1976 Roggenkamp .................... 424/325

OTHER PUBLICATIONS

Sagarin, 1957, pp. 531 to 533, 537 to 539.
Bennett, The Cosmetic Formulary, 1937, pp. 115 to 117, 139 and 141.
Cosmetics & Toiletries, 4/1979, vol. 94, pp. 61 to 69.
Cannelly Cosmetics & Toiletries, 3/1979, vol. 94, pp. 29 to 31.

*Primary Examiner*—Dale R. Ore

[57] ABSTRACT

A composition for use in removing chlorine from hair and a method for using the subject composition to remove chlorine from hair are provided. The subject composition preferably comprises ammonium lauryl sulfate, cocamide diethanolamine, sodium bicarbonate, cocobetaine and water.

11 Claims, No Drawings ated swimming pools have long been aware of the detrimental effects of chlorine on human hair. For competitive swimmers who necessarily spend a large number of hours in swimming pools each week, the problem is especially acute. In many cases, such swimmers have found that their hair actually turns green from chlorine buildup after long term exposure to the chlorinated water.

HAIR TREATMENT PRODUCT

TECHNICAL FIELD

This invention relates to a hair treatment product, and more particularly, to a composition that is useful for removing chlorine from hair. One aspect of the invention relates to a hair treatment product that also functions as a conditioner and is effective when applied to the hair either before or after the application of a permanent wave.

BACKGROUND OF THE INVENTION

Swimmers who spend a great deal of time in and around chlorinated swimming pools have long been aware of the detrimental effects of chlorine on human hair. For competitive swimmers who necessarily spend a large number of hours in swimming pools each week, the problem is especially acute. In many cases, such swimmers have found that their hair actually turns green from chlorine buildup after long term exposure to the chlorinated water.

Although chlorine damage to the hair can be largely avoided by wearing a waterproof, elastomeric swimcap, many swimmers find such caps to be objectionable for other reasons. Swimmers experiencing chlorine damage to their hair have heretofore attempted to wash out the chlorine with conventional, commercially available shampoos, rinses, conditioners, and the like. However, such products have proved to be largely ineffective for treating the chlorine problem.

A composition is therefore needed that can be safely and conveniently applied by an individual to his or her own hair, and that will remove the chlorine from the hair, leaving it manageable and soft.

SUMMARY OF THE INVENTION

According to the present invention, a composition is provided that is adapted to safely and effectively remove chlorine from hair.

According to a preferred embodiment of the invention, a hair treatment product is provided that removes chlorine from the hair and simultaneously conditions chlorine-damaged hair so as to make it more soft and manageable.

According to another embodiment of the invention, a product for removing chlorine from hair is provided that comprises a substantially homogeneous mixture of ammonium lauryl sulfate, cocamide diethanolamine, sodium bicarbonate, cocobetaine and water.

According to a particularly preferred embodiment of the invention, a composition for removing chlorine from hair is provided that comprises from about 2 to about 15 weight percent ammonium lauryl sulfate, from about 2 to about 8 weight percent cocamide diethanolamine, from about 0.1 to about 75 weight percent sodium bicarbonate, from about 2 to about 8 weight percent cocobetaine, and the remainder of water.

According to another preferred embodiment of the invention, minor effective amounts of aloe vera, vitamin D, vitamin E, vitamin C, methylparabens and alcohol are also employed in combination with ammonium lauryl sulfate, cocamide diethanolamine, sodium bicarbonate, cocobetaine and water in the compositions of the invention.

The compositions disclosed herein will, for the first time, provide swimmers with a safe, economical and effective product for removing chlorine from hair and for reconditioning and restoring luster, softness and body to chlorine damaged hair. They can also be effective when utilized as either a preconditioner or postconditioner when applied to the hair before or after treatment with a permanent wave solution.

The compositions of the invention are further described and explained in the detailed description set forth below.

DETAILED DESCRIPTION OF THE INVENTION

The compositions disclosed herein have been found to be surprisingly effective for treating chlorine damaged hair. They are preferably liquid, water-based compositions that can be conveniently applied to the hair and then rinsed out in much the same manner as other conventional, commercially available shampoos and the like. Thus, a swimmer might desirably apply the subject composition to the hair and then rinse it from the hair while showering or bathing in the usual manner upon leaving a chlorinated pool or pool area. After rinsing the subject composition from the hair, the hair can be toweled, blow dried, or otherwise dried, in accordance with the usual preferences of the swimmer.

The compositions of the invention preferably comprise water having dissolved or homogeneously dispersed therein from about 2 to about 15 weight percent ammonium lauryl sulfate, from about 2 to about 8 weight percent cocamide diethanolamine, from about 0.1 to about 75 weight percent sodium bicarbonate and from about 2 to about 8 weight percent cocobetaine. More preferably, the compositions of the invention will comprise water having dissolved or homogeneously dispersed therein from about 2 to about 15 weight percent ammonium lauryl sulfate, from about 2 to about 8 weight percent cocamide diethanolamine, from about 10 to about 20 weight percent sodium bicarbonate, and from about 2 to about 8 weight percent cocobetaine.

Especially desirable results are achieved by employing the foregoing combination of ingredients in combination with minor effective amounts of vitamin C, vitamin D, vitamin E and methylparabens. For most purposes, a minor effective amount of each of the foregoing ingredients ranges up to about 1 percent by weight of the total composition although greater amounts can be included without departing from the scope of the invention. Additionally, relatively minor amounts of an alcohol such as, for example, up to about 2 percent by weight of the nonaqueous ingredients of isopropanol can also be employed in the compositions of the invention to facilitate dissolution and dispersion of the non-water soluble components.

A proteinaceous compound can also be included if desired, and other conventional, commercially available conditioners can be employed to augment the compositions disclosed herein for rehabilitating damaged hair. Thus, although the components recited above are believed to be sufficient for making the compositions of the invention, it will be understood and appreciated by those of ordinary skill in the art upon reading this application that other compounds, components and ingredients can also be incorporated within the subject formulations within the scope of the invention and without otherwise detracting from the unexpected and beneficial results that are achieved with the compositions of the invention. Likewise, it is understood that in some cases other components, compounds or ingredients that are structurally and functionally analagous to those recited above can also be used within the scope of the invention.

The compositions of the present invention are satisfactorily made by mixing the various ingredients at room temperature in a stainless steel tank equipped with a high speed stirring device. After mixing, the composition is transferred by conventional filling equipment into bottles or other containers suitable for shipping, storage or use.

In addition to functioning as a chlorine remover for hair, the subject compositions are also useful when applied before or after treatment with a permanent wave solution, and will make the hair less frizzy following a permanent. Beneficial results have also been observed in using the subject compositions for treatment of hand dermatitis.

Other alterations, modifications or uses of the compositions disclosed herein will become apparent to those of ordinary skill in the art upon reading the specification, and it is intended to cover all such alterations, modifications, or uses as fall within the scope of the appended claims.

What is claimed is:

1. A composition for removing chlorine from hair, said composition comprising from about 2 to about 15 weight percent ammonium lauryl sulfate, from about 2 to about 8 weight percent cocamide diethanolamine, from about 0.1 to about 75 weight percent sodium bicarbonate, from about 2 to about 8 weight percent cocobetaine, and the remainder of water.

2. The composition of claim 1 wherein said sodium bicarbonate is present in an amount ranging from about 2 to about 75 weight percent.

3. The composition of claim 2 wherein said sodium bicarbonate is present in an amount ranging from about 10 to about 20 weight percent.

4. The composition of claim 1, further comprising up to about 2 percent by weight of the nonaqueous ingredients of an alcohol.

5. The composition of claim 4, wherein said alcohol is isopropyl alcohol.

6. The composition of claim 1, further comprising a minor amount of aloe vera.

7. A composition of claim 6 wherein said aloe vera is present in an amount ranging up to about 2 percent by weight of the composition.

8. The composition of claim 1, further comprising a minor amount of methylparabens.

9. The composition of claim 1, further comprising a minor amount of at least one of the vitamins selected from the group consisting of vitamin C, vitamin D, and vitamin E.

10. A method for removing chlorine residuum from hair, said method comprising the steps of:
    a. Wetting hair that contains a chlorine residuum;
    b. Applying to the hair a mixture comprising water, ammonium lauryl sulfate, cocamide diethanolamine, sodium bicarbonate and cocobetaine; and
    c. Thereafter rinsing said hair to remove the chlorine byproducts.

11. The method of claim 10 wherein said mixture further comprises from about 2 to about 15 weight percent ammonium lauryl sulfate, from about 2 to about 8 weight percent cocamide diethanolamine, from about 2 to about 75 weight percent sodium bicarbonate, from about 2 to about 8 weight percent cocobetaine, and the remainder of water.

* * * * *